(12) United States Patent
Hirayama et al.

(10) Patent No.: US 7,358,050 B2
(45) Date of Patent: Apr. 15, 2008

(54) NUCLEIC ACID ADSORBENT; METHODS FOR ADSORBING, REMOVING, DISSOCIATING, AND RECOVERING NUCLEIC ACIDS USING THE SAME; AND METHOD FOR REGENERATING THE SAME

(75) Inventors: Chuichi Hirayama, Kmamoto (JP);
Masayo Sakata, Kumamoto (JP);
Masami Todokoro, Tokyo (JP);
Minoru Nakayama, Minamata (JP)

(73) Assignees: Chisso Corporation, Osaka (JP);
Kumamoto University, Kumamoto (JP)

( * ) Notice: Subject to any disclaimer, the term of this patent is extended or adjusted under 35 U.S.C. 154(b) by 338 days.

(21) Appl. No.: 11/214,773

(22) Filed: Aug. 31, 2005

(65) Prior Publication Data

US 2006/0073499 A1    Apr. 6, 2006

(30) Foreign Application Priority Data

Aug. 31, 2004    (JP)    ............................ 2004-252114
Aug. 24, 2005    (JP)    ............................ 2005-243460

(51) Int. Cl.
*C12Q 1/68*    (2006.01)
*C07H 21/00*    (2006.01)
(52) U.S. Cl. ................ 435/6; 435/5; 435/7.1; 435/7.2; 536/23.1
(58) Field of Classification Search ............ 435/5, 435/6, 7.1, 7.2; 536/23.1
See application file for complete search history.

*Primary Examiner*—Jezia Riley
(74) *Attorney, Agent, or Firm*—Finnegan, Henderson, Farabow, Garrett & Dunner, LLP

(57) ABSTRACT

A nucleic acid adsorbent in which a polymer having a constitutional unit represented by the following formula (I) is immobilized on a water-insoluble carrier is used as a nucleic acid adsorbent capable of selectively and efficiently adsorbing nucleic acids from complex mixtures, such as cell extract,

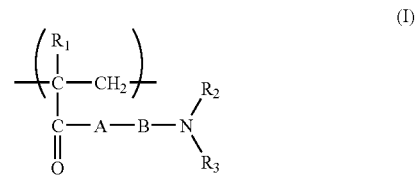

wherein $R_1$ represents hydrogen, fluoride, or methyl; $R_2$ and $R_3$ each independently represent alkyl of 1 to 6 carbon atoms; A is —NH— or —O—; and B represents alkylene of 2 to 18 carbon atoms. Nucleic acids are recovered from cell extract by allowing them to be adsorbed to the nucleic acid adsorbent by mixing this nucleic acid adsorbent with cell extract, removing the nucleic acids from the cell extract by separating the adsorbent therefrom, and dissociating the nucleic acids from the nucleic acid adsorbent by treating the separated nucleic acid adsorbent with alkali.

20 Claims, 4 Drawing Sheets

NUCLEIC ACID ADSORBENT; METHODS FOR ADSORBING, REMOVING, DISSOCIATING, AND RECOVERING NUCLEIC ACIDS USING THE SAME; AND METHOD FOR REGENERATING THE SAME

CROSS REFERENCE TO RELATED APPLICATIONS

This application claims the benefit of priority to Japan Patent Application No. 2004-252114, filed on Aug. 31, 2004, and Japan Patent Application No. 2005-243460, filed on Aug. 24, 2005, both of which are incorporated herein by reference.

BACKGROUND OF THE INVENTION

1. Field of the Invention

The present invention relates to a nucleic acid adsorbent; methods for adsorbing, removing, dissociating, and recovering nucleic acids using the same; and a method for regenerating the same.

2. Description of the Related Art

In recent years, with the increasing development of drugs using biotechnology, useful biologically important substances have been mass-produced by recombinant genes. Drugs produced using recombinant gene technology often contain nucleic acids as impurities. The influence of such nucleic acids on the living body has not been fully clarified. For this reason, FDA and WHO have published guidelines on residual nucleic acids in biologicals. According to the guideline of WHO, it is desirable that the amount of residual nucleic acids in an adult dose should be not more than 10 ng (WEEKLY EPIDEMIOLOGICAL RECORD, No. 20, 16, MAY, 1997).

Methods for removing nucleic acids have been known: One example is the technique of eliminating nucleic acids by aggregation and precipitation using a water-soluble nucleic acid adsorbent. The nucleic acid adsorbent is protamine sulfuric acid or streptomycin ("Biochemical Experiment Lecture 5," p. 201, edited by the Japanese Biochemical Society, published by Tokyo Kagaku Dojin). Another nucleic acid adsorbent is cationic hydroxyalkylcellulose (Japanese Laid-Open Application No. 1989-25791). However, this method requires, when aggregation treatment is performed on the water-soluble adsorbent, the operations of removing aggregates by centrifugation and then removing a soluble flocculating agent that has been added in excess.

The chromatography techniques, such as ion exchange, gel filtration, and affinity chromatography, have also been considered. These techniques have several problems, such as a low nucleic acid removal rate, a low removal of the target biological substance, complicated setting of removal conditions, inadequate mechanical strength of chromatography agents, none of which are preferred for industrial use. For example, in the method for removing nucleic acids by adsorption with chitosan, when the pH of the solution containing nucleic acids is basic, the ability to remove nucleic acids is reduced (Japanese Laid-Open Application No. 1991-109397 and Japanese Laid-Open Application No. 1991-109940).

SUMMARY OF THE INVENTION

The present inventors have intensively studied to solve the above-mentioned problems and, as a result, found that the adsorbent described below has the ability to selectively adsorb nucleic acids. The present invention has thus been accomplished as follows:

(1) a nucleic acid adsorbent for adsorbing a nucleic acid contained in cell extract, in which a polymer including a constitutional unit represented by the following formula (I) is immobilized on a water-insoluble carrier, in which $R_1$ represents hydrogen, fluoride, or methyl; $R_2$ and $R_3$ each independently represent alkyl of 1 to 6 carbon atoms; A represents —NH— or —O—; and B represents alkylene of 2 to 18 carbon atoms;

(2) the nucleic acid adsorbent of (1), in which, in formula (I), R1 represents hydrogen or methyl; $R_2$ and $R_3$ each independently represent methyl, ethyl, or propyl; A represents —NH— or —O—; and B represents alkylene of 2 to 6 carbon atoms;

(3) the nucleic acid adsorbent of (1), in which, in formula (I), R1 represents hydrogen or methyl; $R_2$ and $R_3$ each independently represent methyl or ethyl; A represents —NH— or —O—; and B represents propylene;

(4) the nucleic acid adsorbent of (1), in which, in formula (I), $R_1$ represents hydrogen; $R_2$ and $R_3$ represent methyl; A represents —NH—; and B represents propylene;

(5) the nucleic acid adsorbent of (1), in which, in formula (I), $R_1$ represents methyl; $R_2$ and $R_3$ represent methyl; A represents —NH—; and B represents propylene;

(6) a nucleic acid adsorbent for adsorbing a nucleic acid contained in cell extract, in which a polymer formed from one monomer represented by the following formula (II) is immobilized on a water-insoluble carrier, in which $R_1$ represents hydrogen, fluoride, or methyl; $R_2$ and $R_3$ each independently represent alkyl of 1 to 6 carbon atoms; A represents —NH— or —O—; and B represents alkylene of 2 to 18 carbon atoms;

(7) a nucleic acid adsorbent for adsorbing a nucleic acid contained in cell extract, in which a polymer formed from a mixture including at least one monomer represented by the following formula (II) is immobilized on a water-insoluble carrier, in which $R_1$ represents hydrogen, fluoride, or methyl; $R_2$ and $R_3$ each independently represent alkyl of 1 to 6 carbon atoms; A represents —NH— or —O—; and B represents alkylene of 2 to 18 carbon atoms;

(8) the nucleic acid adsorbent of (6) or (7), in which, in formula (II), $R_1$ represents hydrogen or methyl; $R_2$ and $R_3$ each independently represent methyl, ethyl, or propyl; A represents —NH— or —O—; and B represents alkylene of 2 to 6 carbon atoms;

(9) the nucleic acid adsorbent of (6) or (7), in which, in formula (II), $R_1$ represents hydrogen or methyl; $R_2$ and $R_3$ represent methyl; A represents —NH— or —O—; and B represents alkylene of 2 to 6 carbon atoms;

(10) the nucleic acid adsorbent of (6) or (7), in which, in formula (II), $R_1$ represents hydrogen; $R_2$ and $R_3$ represent methyl; A represents —NH—; and B represents propylene;

(11) the nucleic acid adsorbent of (6) or (7), in which, in formula (II), $R_1$ represents methyl; $R_2$ and $R_3$ represent methyl; A represents —NH—; and B represents propylene;

(12) the nucleic acid adsorbent of (7), in which the polymer formed from the mixture further including at least one monomer represented by the following formula (III) is immobilized on the water-insoluble carrier, (III)

in which, $R_4$ represents hydrogen or methyl; $R_5$, $R_6$, and $R_7$ each independently represent alkyl of 1 to 3 carbon atoms, D represents —NH— or —O—, E represents alkylene of 2 to 6 carbon atoms, and X represents fluoride, chlorine, bromine, iodine, $1/2SO_4$, $1/3PO_4$, $1/2CO_3$, or $NO_2$;

(13) the nucleic acid adsorbent of (7), in which the polymer formed from the mixture further including at least one monomer represented by the following formula (IV) is immobilized on the water-insoluble carrier, (IV)

in which $R_8$ represents hydrogen or methyl; $R_9$ represents alkyl of 1 to 3 carbon atoms; G represents —NH—, —$NR_{10}$—, or —O—; and $R_{10}$ represents alkyl of 1 to 3 carbon atoms;

(14) the nucleic acid adsorbent one of (1) to (13), in which the polymer is immobilized on the water-insoluble carrier with a crosslinker;

(15) the nucleic acid adsorbent of (14), in which the crosslinker is epichlorohydrin;

(16) the nucleic acid adsorbent of one of (1) to (15), in which the water-insoluble carrier is in the form of a sphere, hollow fiber, or membrane;

(17) the nucleic acid adsorbent of one of (1) to (16), in which the water-insoluble carrier is cellulose;

(18) the nucleic acid adsorbent of (17), in which the cellulose is a spherical particle;

(19) the nucleic acid adsorbent of one of (1) to (18), in which the cell extract is yeast extract;

(20) a method for adsorbing a nucleic acid contained in cell extract, in which the nucleic acid adsorbent of one of (1) to (19) is mixed with a solution containing a nucleic acid;

(21) a method for removing a nucleic acid contained in cell extract, including separating from the cell extract the nucleic acid adsorbent that has adsorbed the nucleic acid by the adsorption method of (20);

(22) the method of (20) or (21), in which the cell extract is yeast extract;

(23) a method for dissociating a nucleic acid from a nucleic acid adsorbent that has adsorbed the nucleic acid in a solution and in which a polymer including a constitutional unit represented by the following formula (I) is immobilized on a water-insoluble carrier, wherein the ionic strength of the solution is in the range of 0.3 or more to 3.0 or less, (I)

in which $R_1$ represents hydrogen, fluoride, or methyl; $R_2$ and $R_3$ each independently represent alkyl of 1 to 6 carbon atoms; A represents —NH— or —O—; and B represents alkylene of 2 to 18 carbon atoms.

24. a method for dissociating a nucleic acid from a nucleic acid adsorbent that has adsorbed the nucleic acid in a solution and in which a polymer formed from one monomer represented by the following formula (II) is immobilized on a water-insoluble carrier, in which the ionic strength of the solution is in the range of 0.3 or more to 3.0 or less, (II)

in which $R_1$ represents hydrogen, fluoride, or methyl; $R_2$ and $R_3$ each independently represent alkyl of 1 to 6 carbon atoms; A represents —NH— or —O—; and B represents alkylene of 2 to 18 carbon atoms;

(25) a method for dissociating a nucleic acid from a nucleic acid adsorbent that has adsorbed the nucleic acid in a solution and in which a polymer formed from a mixture including at least one monomer represented by the following formula (II) is immobilized on a water-insoluble carrier, in which the ionic strength of the solution is in the range of 0.3 or more to 3.0 or less, (II)

in which $R_1$ represents hydrogen, fluoride, or methyl; $R_2$ and $R_3$ each independently represent alkyl of 1 to 6 carbon atoms; A represents —NH— or —O—; and B represents alkylene of 2 to 18 carbon atoms;

(26) a method for dissociating a nucleic acid from the nucleic acid adsorbent of (25) that has adsorbed the nucleic acid in a solution and in which a polymer formed from a mixture further including at least one monomer represented by the following formula (III) is immobilized on a water-insoluble carrier, in which the ionic strength of the solution is in the range of 0.3 or more to 3.0 or less, (III)

in which, $R_4$ represents hydrogen or methyl; $R_5$, $R_6$, and $R_7$ each independently represent alkyl of 1 to 3 carbon atoms; D represents —NH— or —O—; E represents alkylene of 2 to 6 carbon atoms; and X represents fluoride, chlorine, bromine, iodine, $1/2SO_4$, $1/3PO_4$, $1/2CO_3$, or $NO_2$;

(27) a method for dissociating a nucleic acid from the nucleic acid adsorbent of (25) that has adsorbed the nucleic acid in a solution and in which a polymer formed from a mixture further including at least one monomer represented by the following formula (IV) is immobilized on a water-insoluble carrier, in which the ionic strength of the solution is in the range of 0.3 or more to 3.0 or less, (IV)

in which $R_8$ represents hydrogen or methyl; $R_9$ represents alkyl of 1 to 3 carbon atoms; G represents —NH—, —$NR_{10}$—, or —O—; and $R_{10}$ represents alkyl of 1 to 3 carbon atoms;

(28) the method of one of (23) to (27), in which the ionic strength is in the range of 0.6 or more to 1.2 or less;

(29) the method of one of (23) to (28), in which the solution is cell extract;

(30) a method for recovering a nucleic acid from cell extract, the method including:
  allowing the nucleic acid to be adsorbed to the nucleic acid adsorbent by the method for absorbing a nucleic acid of (20);
  separating the nucleic acid adsorbent that has adsorbed the nucleic acid from the cell extract by the method for removing a nucleic acid of (21);
  dissociating the nucleic acid from the nucleic acid adsorbent that has adsorbed the nucleic acid by the method for dissociating a nucleic acid of one of (23) to (28); and
  separating the nucleic acid adsorbent that has been dissociated;

(31) the method of (29) or (30), in which the cell extract is yeast extract;

(32) a method for regenerating a nucleic acid adsorbent in which a polymer including a constitutional unit represented by the following formula (I) is immobilized on a water-insoluble carrier, in which the nucleic acid adsorbent used for recovering a nucleic acid is washed with an alkaline solution, (I)

in which $R_1$ represents hydrogen, fluoride, or methyl; $R_2$ and $R_3$ each independently represent alkyl of 1 to 6 carbon atoms; A represents —NH— or —O—; and B represents alkylene of 2 to 18 carbon atoms;

(33) a method for regenerating a nucleic acid adsorbent in which a polymer formed from one monomer represented by the following formula (I) is immobilized on a water-insoluble carrier, in which the nucleic acid adsorbent used for recovering a nucleic acid is washed with an alkaline solution, (II)

in which $R_1$ represents hydrogen, fluoride, or methyl; $R_2$ and $R_3$ each independently represent alkyl of 1 to 6 carbon atoms; A represents —NH— or —O—; and B represents alkylene of 2 to 18 carbon atoms;

(34) a method for regenerating a nucleic acid adsorbent in which a polymer formed from a mixture including at least one monomer represented by the following formula (II) is immobilized on a water-insoluble carrier, in which the nucleic acid adsorbent used for recovering a nucleic acid is washed with an alkaline solution, (II)

in which $R_1$ represents hydrogen, fluoride, or methyl; $R_2$ and $R_3$ each independently represent alkyl of 1 to 6 carbon atoms; A represents —NH— or —O—; and B represents alkylene of 2 to 18 carbon atoms;

(35) the method for regenerating a nucleic acid adsorbent of (34) in which the polymer formed from the mixture further including at least one monomer represented by the following formula (III) is immobilized on the water-insoluble carrier, in which the nucleic acid adsorbent used for recovering the nucleic acid is washed with the alkaline solution, (III)

in which, $R_4$ represents hydrogen or methyl; $R_5$, $R_6$, and $R_7$ each independently represent alkyl of 1 to 3 carbon atoms; D represents —NH— or —O—; E represents alkylene of 2 to 6 carbon atoms; and X represents fluoride, chlorine, bromine, iodine, $1/2SO_4$, $1/3PO_4$, $1/2CO_3$, or $NO_2$;

(36) the method for regenerating a nucleic acid adsorbent of (34) in which the polymer formed from the mixture further including at least one monomer represented by the following formula (IV) is immobilized on the water-insoluble carrier, in which the nucleic acid adsorbent used for recovering the nucleic acid is washed with the alkaline solution, (IV)

in which $R_8$ represents hydrogen or methyl; $R_9$ represents alkyl of 1 to 3 carbon atoms; G represents —NH—, —$NR_{10}$—, or —O—; and $R_{10}$ represents alkyl of 1 to 3 carbon atoms.

(37) the method of one of (28) to (30), in which the pH of the alkaline solution is 12 or higher; and (38) a method for recovering a nucleic acid from cell extract multiple times by using a nucleic acid adsorbent multiple times, the method including:

separating the nucleic acid adsorbent in the method for recovering a nucleic acid of (30);

regenerating the nucleic acid adsorbent by the method for regenerating a nucleic acid adsorbent of one of (34) to (37); and reusing the nucleic acid adsorbent that has been regenerated.

BRIEF DESCRIPTION OF THE DRAWINGS

The invention, together with further advantages thereof, may best be understood by reference to the following description taken in conjunction with the accompanying drawings in which.

DETAILED DESCRIPTION OF THE PREFERRED EMBODIMENTS

The object, characteristics, and advantages of the present invention as well as the idea thereof will be apparent to those skilled in the art from the descriptions given herein. It is to be understood that the embodiments and specific examples of the invention described herein below are to be taken as preferred examples of the present invention. These descriptions are only for illustrative and explanatory purposes and are not intended to limit the invention to these embodiments or examples. It is further apparent to those skilled in the art that various changes and modifications may be made based on the descriptions given herein within the intent and scope of the present invention disclosed herein.

==Nucleic Acid Adsorbent ==

A "polymer that has a constitutional unit represented by formula (I)" is in some contexts described as a "polymer (I)." A "monomer represented by formula (II)," etc. is in some contexts described as a "monomer (II)," etc. (Meta) acrylamide refers either to acrylamide or to meta-acrylamide. (Meta)acrylic ester, etc. should also be read in the same manner.

The nucleic acid adsorbent according to the present invention is an adsorbent in which a polymer (I) that contains a constitutional unit having dialkylamino group(s) is immobilized on a water-insoluble carrier. For immobilization, a crosslinker or the like can be used. A polymer (I) can be a homopolymer of a monomer (II), a copolymer of monomers (II), a copolymer of a monomer (II) and another monomer (other monomers), etc. Examples of other monomers include a monomer (III), a monomer (IV), etc. The starting material for a monopolymer is one monomer (II). The starting material for a copolymer is a mixture of a plurality of monomers. To polymerize monomers, a polymerization initiator and a solvent may be used. Hereinbelow, monomers, types of polymers, conditions for polymerization of monomers, polymerization initiators, solvents to be used for polymerization, water-insoluble carriers, and immobilization of polymers (crosslinkers), molecular weights and pKa of polymers, etc. will be sequentially explained specifically.

Monomers (II) is (meta)acrylamides or (meta)acrylic esters. These monomers have dialkylamino. Examples of monomers having dimethylamino include N,N-dimethylaminoethyl (meta)acrylamide, N,N-dimethylaminopropyl (meta)acrylamide, N,N-dimethylaminobutyl (meta)acrylamide, N,N-dimethylaminopentyl (meta)acrylamide, N,N-dimethylaminohexyl (meta)acrylamide, etc. Examples of monomers having diethylamino include N,N-diethylaminoethyl (meta)acrylamide, N,N-diethylaminopropyl (meta) acrylamide, N,N-diethylaminobutyl (meta)acrylamide, N,N-diethylaminopentyl (meta)acrylamide, N,N-diethylaminohexyl (meta)acrylamide, etc.

Further examples of monomers having amino include N,N-dipropylaminopropyl (meta)acrylamide, N,N-dipropylaminobutyl (meta)acrylamide, N,N-dipropylaminopentyl (meta)acrylamide, N,N-dipropylaminohexyl (meta)acrylamide, etc.

Examples of (meta)acrylic esters include N,N-dimethylaminoethyl (meta)acrylate, N,N-dimethylaminopropyl (meta)acrylate, N,N-dimethylaminobutyl (meta)acrylate, N,N-dimethylaminopentyl (meta)acrylate, N,N-dimethylaminohexyl (meta)acrylate, N,N-diethylaminoethyl (meta)acrylate, etc. A preferred monomer (II) is N,N-dimethylaminopropyl (meta)acrylamide.

Monomer (III) is the quaternary ammonium salt of (meta) acrylamide or (meta)acrylic ester. Examples of amide salts include 2-(meta)acrylamide-ethyltrimethyl ammonium chloride, 3-(meta)acrylamide-propyltrimethyl ammonium chloride, 4-(meta)acrylamide-butyltrimethyl ammonium chloride, 5-(meta)acrylamide-pentyltrimethyl ammonium chloride, 6-(meta)acrylamide-hexyltrimethyl ammonium chloride, etc.

Examples of ester salts include 2-(meta)acryloyl-oxyethyltrimethyl ammonium chloride, 3-(meta)acryloyl-oxypropyltrimethyl ammonium chloride, 4-(meta)acryloyl-oxybutyltrimethyl ammonium chloride, 5-(meta)acryloyl-oxypentyltrimethyl ammonium chloride, 6-(meta)acryloyl-oxyhexyltrimethyl ammonium chloride, etc.

Monomers (IV) are other (meta)acrylamides or (meta) acrylic esters. Examples of such amide include (meta) acrylamide, N,N-dimethyl(meta)acrylamide, N-propyl (meta)acrylamide, N-isopropyl(meta)acrylamide, etc. Examples of such ester include (meta)methyl acrylate, (meta)ethyl acrylate, (meta)propyl acrylate, etc.

A homopolymer is prepared from a single monomer (II). A copolymer is prepared from a mixture of at least two monomers (II). A copolymer is also prepared from a mixture containing at least a single monomer (II). The other monomers (another monomer) in this mixture are (is) monomers (a monomer) different from monomers (II). Examples of the other monomers (another monomer) include a monomer (III), a monomer (IV), etc. The mixture may contain either a monomer (III) and/or a monomer (IV) The mixture may contain a monomer that does not categorized as a monomer (III) or a monomer (IV). The proportion of a monomer (II) in these mixtures is preferably 10 mol % or more, and more preferably 50 mol % or more. This mixture may consist only of a plurality of monomers (II). When single monomers (II) or a mixture containing a monomer (II) are (is) polymerized, a polymerization initiator, a solvent, etc. may be added if necessary.

Examples of polymerization reactions include known aqueous polymerization, suspension polymerization, emulsion polymerization, etc. From an industrial viewpoint, a preferable reaction is aqueous polymerization. The reaction temperature is preferably 0° C. to 80° C., more preferably 10° C. to 50° C. The reaction is typically performed at room temperature (20° C. to 30° C.). The reaction time is preferably about 3 to 10 hours.

Examples of the polymerization initiator include azo compounds, superoxides, etc. A redox compound, which combines a superoxide and a reducing agent, may be used. Examples of azo compounds include 2,2'-azobisisobutyronitrile 2,2'-azobis(2,4-dimethylvaleronitrile), 1,1'-azobis(cyclohexane-1-carbonitrile), 2,2'-azobisisobutyric acid dimethyl, etc. Examples of superoxides include hydrogen peroxide, lauroyl peroxide, benzoyl peroxide, potassium persulfate, ammonium persulfate, sodium chlorate, etc. A preferred polymerization initiator is potassium persulfate or ammonium persulfate.

Examples of the polymerization solvent include water, dimethylformamide, dimethylacetamide, N-methyl pyrolidone, dimethylsulfoxide, acetonitrile, tetrahydrofuran, dioxane, etc. A preferred solvent is water. A preferred monomer concentration range is from 0.1 wt % to 50 wt %, with a more preferred range being from 1 wt % to 20 wt %.

Examples of the water-insoluble carrier include water-insoluble polysaccharides, such as cellulose, agarose, chitin, starch, etc. Other examples are homopolymers and copolymers, which are formed from monomers, such as acrylamides, methacrylamides, acrylics, methacryls, vinyls, allyls, etc. When polysaccharides, such as a cellulose, agarose, chitin, chitosan, and starch, are water-soluble, they may be made water-insoluble by treatment of a crosslinking reaction or the like. The treatment of a crosslinking reaction or the like may be performed for the purpose of enhancing physical strength. Examples of a preferred carrier include cellulose etc.

Forms of the water-insoluble carrier include, but not limited to, particles, strings, membranes, etc. Preferred shapes are the forms of spheres, hollow fibers, membranes, etc. A preferred shape of particles is the spherical form. Spherical particles are easy to fabricate and handle. A preferred shape of strings is the hollow fiber form. The hollow fiber form refers to a fibrous form having continuous or discontinuous hollows therein. The hollows are formed by adding foaming agent to a spinning dope or by using a special spinneret or the like. A preferred shape of membranes is the porous form. Porous membranes, such as commercially available membrane filters, have a certain range of exclusion limit of molecular weight. Among these, a preferred carrier is spherical cellulose particles. This kind of particles is inexpensive, with high biocompatibility and strength as well as good column resistance to pressure.

When polymer (I) is immobilized on a water-insoluble carrier, the nucleophilicity of dialkylamino of polymer (I) is used. The water insoluble carrier is pretreated so that it is reactive to dialkylamino. This pretreatment is performed using a crosslinker etc. The crosslinker is a compound or the like that has a plurality of reactive functional groups. Examples of bifunctional compounds include alkyl dihalide compounds, a diepoxides, alkanediol diglycidyl ether compounds, alkyl halide epoxide compounds, etc. Examples of trifunctional compounds include alkane trihalide compounds, an alkanetriol diglycidyl ether compounds, etc.

Examples of alkyl dihalide compounds include 1, 3-dichloropropane, 1,4-dichlorobutane, 1,5-dichloropentane, 1,6-dichlorohexane, 1,7-dichloroheptane, 1,8-dichlorooctane, etc. Examples of diepoxide compounds include 1,2,3,4-diepoxybutane, 1,2,4,5-diepoxypentane, 1,2,5,6-diepoxyhexane, 1,2,6,7-diepoxyheptane, 1,2,7,8-diepoxyoctane, 1,2,8,9-diepoxynonane, 1,2,9,10-diepoxydecane, etc.

Examples of alkanediol diglycidyl ether compounds include ethylene glycol diglycidyl ether, 1,3-propanediol diglycidyl ether, 1,4-butanediol diglycidyl ether, 1,5-pentanediol diglycidyl ether, 1,6-dihydroxyhexane diglycidyl ether, etc. Examples of the alkyl halide epoxide compound include epichlorohydrin, 1-chloro-3,4-epoxy butane, 1-chloro-4,5-epoxy pentane, 1-chloro-5,6-epoxy hexane, etc.

Examples of alkane trihalide compounds include 2-chloromethyl-1,3-dichloropropane, 2-chloroethyl-1, 3-dichloropropane, etc. Examples of alkanetriol diglycidyl ethers include glycol triglycidyl ether, trimethylolethane triglycidyl ether, trimethylol propane triglycidyl ether, etc.

Among these polyfunctional compounds, a preferred crosslinker is ethylene glycol diglycidyl ether, 1,3-propanediol diglycidyl ether, or epichlorohydrin, a more preferred crosslinker being epichlorohydrin, which is suitable for controlling immobilization, thus facilitating the preparation of a nucleic acid adsorbent.

The nucleic acid adsorbent according to the present invention selectively adsorbs nucleic acids. This high selectivity is based on factors, such as the molecular weight and pKa of a polymer (I). Appropriate setting of these factors enables control of hydrophilicity and hydrophobicity on the surface of the nucleic acid adsorbent. This control can reduce the interaction between biological substances, such as proteins, and the nucleic acid adsorbent.

The molecular weight of polymer (I) is the weight average molecular weight based on polyethylene oxide obtained by gel permeation chromatography (GPC). The molecular weight of polymer (I) is typically 1,000 to 5,000,000, preferably 5,000 to 3,000,000, more preferably 10,000 to 1,000,000, still more preferably 100,000 to 2,000,000.

Polymer (I) is basic because it contains nitrogen. pKa of polymer (I) is typically 7.2 to 10.4, preferably 7.4 to 9.5, more preferably 7.5 to 9.0.

Here, nucleic acid to be adsorbed by the adsorbent according to the present invention may be any of DNA, RNA, chimeric DNA-RNA molecules, oligonucleotides, polynucleotides, mixtures thereof, etc., and the composition, length, etc. thereof are not particularly limited.

==Adsorption and Removal of Nucleic Acids, and Dissociation and Recovery Thereof from the Adsorbent==

Use of the nucleic acid adsorbent according to the present invention enables selective adsorption of nucleic acids. A nucleic acid adsorbent that has adsorbed nucleic acids can be easily taken out of the system because the adsorbent is polymer (I) immobilized on a water-insoluble carrier. Further, nucleic acids can be dissociated from the nucleic acid adsorbent that has adsorbed the nucleic acids. The nucleic acids that have been dissociated can easily be separated and recovered from the nucleic acid adsorbent. Therefore, this methods is effective in removing or recovering nucleic acids contained in biological substances useful as drugs, such as proteins, enzymes, and physiologically active substances, as well as nucleic acids contained in complex mixtures, such as cell extracts.

The following will specifically explain the methods for adsorption and removal of nucleic acids in a solution containing nucleic acids and then dissociation and recovery of the nucleic acids from the adsorbent by using the nucleic acid adsorption described above. The nucleic acid adsorbent should be prewashed with a suitable buffer prior to adsorption treatment. The nucleic acid adsorbent adsorbs nucleic acids when it is mixed with a solution containing nucleic acids. Thus, by removing from the solution the nucleic acid adsorbent that has adsorbed nucleic acids, it is possible to remove nucleic acids themselves from the solution. For example, in a batch method, the nucleic acid adsorbent washed with a buffer is added to a nucleic acid-containing solution and mixed in a test tube or the like and then the nucleic acid adsorbent is separated. This separation is performed by filtration or the like. In a column method, a column packed with the nucleic acid adsorbent is washed with a buffer and then a nucleic acid-containing solution is passed through. Since nucleic acids are adsorbed onto the column by this methods, an effluent from which nucleic acids has been removed can be obtained. Here, a phosphate buffer, Tris buffer, etc. can be used as a buffer.

The nucleic acid adsorbent that has thus adsorbed nucleic acids and been separated from the solution is washed with a suitable buffer. In order to recover nucleic acids, it is necessary to wash the adsorbent with nucleic acids attached on the adsorbent. For this purpose, an aqueous solution with an ionic strength of 0.9 or less, more preferably 0.4 or less, may be used. In this case, to remove contaminants, other than nucleic acids, attached on the nucleic acid adsorbent, a salt solution with an ionic strength of 0.2 or more is preferably used. Subsequently, nucleic acids are dissociated from the nucleic acid adsorbent by treating nucleic acids with a salt solution with an ionic strength of 0.3 or more to 3.0 or less, more preferably 0.6 or more to 1.2 or less. For example, in a batch method, nucleic acids can be recovered by washing the nucleic acid adsorbent that has adsorbed nucleic acids with a salt solution with an ionic strength of 0.2 or more to 0.4 or less, prior to separating nucleic acids from the nucleic acid adsorbent by suspending the nucleic acid adsorbent that has adsorbed nucleic acids with a salt solution with an ionic strength of 0.6 or more to 1.2 or less, followed by centrifugation to recover the supernatant. In a column method, nucleic acids can be separated and recovered by washing the column by passing a suitable volume of a salt solution with an ionic strength of 0.2 or more to 0.4 or less through the column to which nucleic acids have been adsorbed, followed by eluting the nucleic acids with a salt solution with an ionic strength of 0.6 or more to 1.2 or less. Here, as the salt solution, sodium chloride, potassium chloride, ammonium chloride, sodium sulfate, potassium sulfate, ammonium sulfate, etc. can be used, and their type is not particularly limited.

The nucleic acid adsorbent that has been used in this manner can be regenerated by removing the residual nucleic acids by washing with an alkaline solution, followed by washing with a buffer. As the alkaline solution, sodium hydroxide, potassium hydroxide, etc. can be used, and their type is not particularly limited. Since a sodium hydroxide has a pH of 13.0, 12.6, and 11.8 at 0.2 M, 0.05 M, and 0.01 M, respectively, an alkaline solution of pH 12 or higher is preferably used, more preferably, of pH 13.0 or higher. The nucleic acid adsorbent regenerated in this manner can be reused to recover nucleic acids. This regeneration and recovery can be repeated at least 5 times.

EXAMPLES

Hereinafter, the present invention will be explained in more detail with reference to Examples and Comparative examples. However, the present invention is by no means limited by these Examples. The pH, concentration, and ionic strength of the phosphate buffer used in the experiments are, unless otherwise described, 7, 0.02 M, and 0.2, respectively. Here, the ionic strength was adjusted to a given value by adding sodium chloride to 0.02 M phosphate buffer (pH 7).

Example 1

Preparation of the polymer of
N,N-dimethylaminopropylacrylamide

The reaction was performed under nitrogen atmosphere. Ion exchange water (328 g) and N,N-dimethylaminopropylacrylamide (18.0 g) were mixed in a 1 L three-necked flask equipped with a stirrer, thermometer, and nitrogen inlet tube. To this mixture was added a 5.0% ammonium persulfate aqueous solution (14.4 g), followed by stirring at room temperature for 16 hours to afford an aqueous solution of a polymer. The weight average molecular weight of this polymer was measured by gel permeation chromatography (GPC; on the basis of polyethylene oxide) and found to be 300,000.

Example 2

Preparation Nucleic Acid Adsorbent A

A mixture of cellulose particles with a mean particle diameter of 80 μm (300 g; water: 90 wt %, dry weight: 30.5 g) with an exclusion limit molecular weight of 2,000,000, as determined using polyethylene oxide as reference material, and ion exchange water (410 g) was warmed to 30° C. To this mixture was added a 20% aqueous sodium hydroxide (227 g), followed by stirring for 1 hour. Subsequently, epichlorohydrin (131 g) was added and the mixture was reacted for 2 hours. The reaction mixture was filtrated and then washed until the resulting epoxy-activated cellulose particles became neutral. Next, epoxy-activated cellulose particles (100 g; wet weight) were added and mixed in the aqueous solution (150 g) of the polymer of N,N-dimethylaminopropylacrylamide prepared in Example 1, and the mixture was reacted at 45° C. for 16 hours. The resulting reacted mixture was filtrated and washed until the adsorbent became neutral. The adsorbent thus obtained is called adsorbent A.

Example 3

Adsorption of Nucleic Acids to Adsorbent A and removal Thereof from a Nucleic Acid Solution by a Batch Method A mixture of adsorbent A (0.50 g) and 10 mL of phosphate buffer was stirred at room temperature for 10 min. After equilibration in this manner, adsorbent A equilibrated with the buffer was obtained by filtration. This adsorbent A was mixed with a solution of nucleic acid from salmon testes (DNA; 50 μg) plus bovine serumn albumin (BSA; 5000 μg) in phosphate buffer (5 mL), followed by stirring at 25° C. for 2 hours. After stirring, the concentration of DNA in the supernatant was measured and found to be 50 ng/mL or lower (DNA adsorption: 99.5% or higher). The concentration of BSA in the supernatant was measured and found to be 830 μg/mL (BSA recovery: 83%)

Example 4

Adsorption of Nucleic Acids to Adsorbent A and Removal Thereof from a Nucleic Acid Solution by a Chromatography Method The column (diameter: 4.6 mm, length: 100 mm) packed with adsorbent A (1.67 mL) was equilibrated by passing through phosphate buffer. Subsequently, a solution of nucleic acid from salmon testes (DNA; 1 mg) and bovine serum albumin (BSA; 100 mg) in phosphate buffer (100 mL) was passed through the column to give 100 mL of effluent. The DNA concentration and the BSA concentration of the effluent were 0.3 μg/mL or lower (DNA adsorption: 97% or higher) and 960 μg/mL (BSA recovery: 96%), respectively.

Example 5

Preparation of Nucleic Acid Adsorbent B

A mixture of ion exchange water (508 g) and cellulose particles with a mean particle diameter of 80 μm (250 g; water: 46 wt %, dry weight: 134 g) with an exclusion limit molecular weight of 1,000, as determined using polyethylene oxide as a standard substance was warmed to 30° C. To this mixture was added a 20% aqueous sodium hydroxide (207 g), followed by stirring for 1 hour. Subsequently, epichlorohydrin (131 g) was added and the mixture was reacted for 2 hours. The resulting reacted mixture was filtrated and then washed until the resulting epoxy-activated cellulose particles became neutral. Next, epoxy-activated cellulose particles (100 g; wet weight) were mixed with the aqueous solution (150 g) of the polymer of N,N-dimethylaminopropylacrylamide prepared in Example 1, and the mixture was reacted at 45° C. for 16 hours. The resulting reaction mixture was filtrated and washed until the adsorbent became neutral. The adsorbent thus obtained is called adsorbent B.

Example 6

Adsorption of Nucleic Acids to Adsorbent B and removal Thereof from a Nucleic Acid Solution by a Batch Method A mixture of adsorbent B (0.50 g) and 10 mL of phosphate buffer was stirred at room temperature for 10 min. After equilibration in this manner, adsorbent B equilibrated with the buffer was obtained by filtration. This adsorbent B was mixed with a solution of nucleic acid from salmon testes (DNA; 50 μg) plus bovine serum albumin (BSA; 5000 μg) in phosphate buffer (5 mL), followed by stirring at 25° C. for 2 hours. After stirring, the concentration of DNA in the supernatant was measured and found to be 0.1 μg/mL or lower (DNA adsorption: 99% or higher). The concentration of BSA in the supernatant was measured and found to be 970 μg/mL (BSA recovery: 97%)

COMPARATIVE EXAMPLE

Nucleic acids were removed by a batch method using DEAE-Sepharose CL-6B (an anion exchanger from Amersham Biosciences). DEAE-Sepharose CL-6B (0.50 g) was mixed with 10 mL of phosphate buffer, followed by stirring at room temperature for 10 min. After equilibration in this manner, the ion exchanger was recovered by filtration. This DEAE-Sepharose CL-6B was mixed with a solution (5 mL) of nucleic acid (DNA; 50 μg) and bovine serum albumin (BSA; 2500 μg) in phosphate buffer, followed by stirring at 25° C. for 2 hours. After stirring, the concentration of DNA in the supernatant was measured and found to be 2 μg/mL. The concentration of BSA in the supernatant was measured and found to be 470 μg/mL (recovery: 94%).

Example 7

Adsorption of Nucleic Acids to Adsorbent B and Removal Thereof from a Nucleic Acid Solution by a Chromatography Method The column (diameter: 4.6 mm, length: 100 mm) packed with adsorbent B (1.67 mL) was equilibrated by passing through phosphate buffer. Subsequently, a solution of nucleic acid (DNA; 1 mg) and bovine serum albumin (BSA; 100 mg) in phosphate buffer (100 mL) was passed through the column to give 100 mL of effluent. The DNA and BSA concentrations of the effluent were 0.1 μg/mL or lower (DNA adsorption: 99% or higher) and 950 μg/mL (BSA recovery: 95%), respectively.

Example 8

Figure 1:
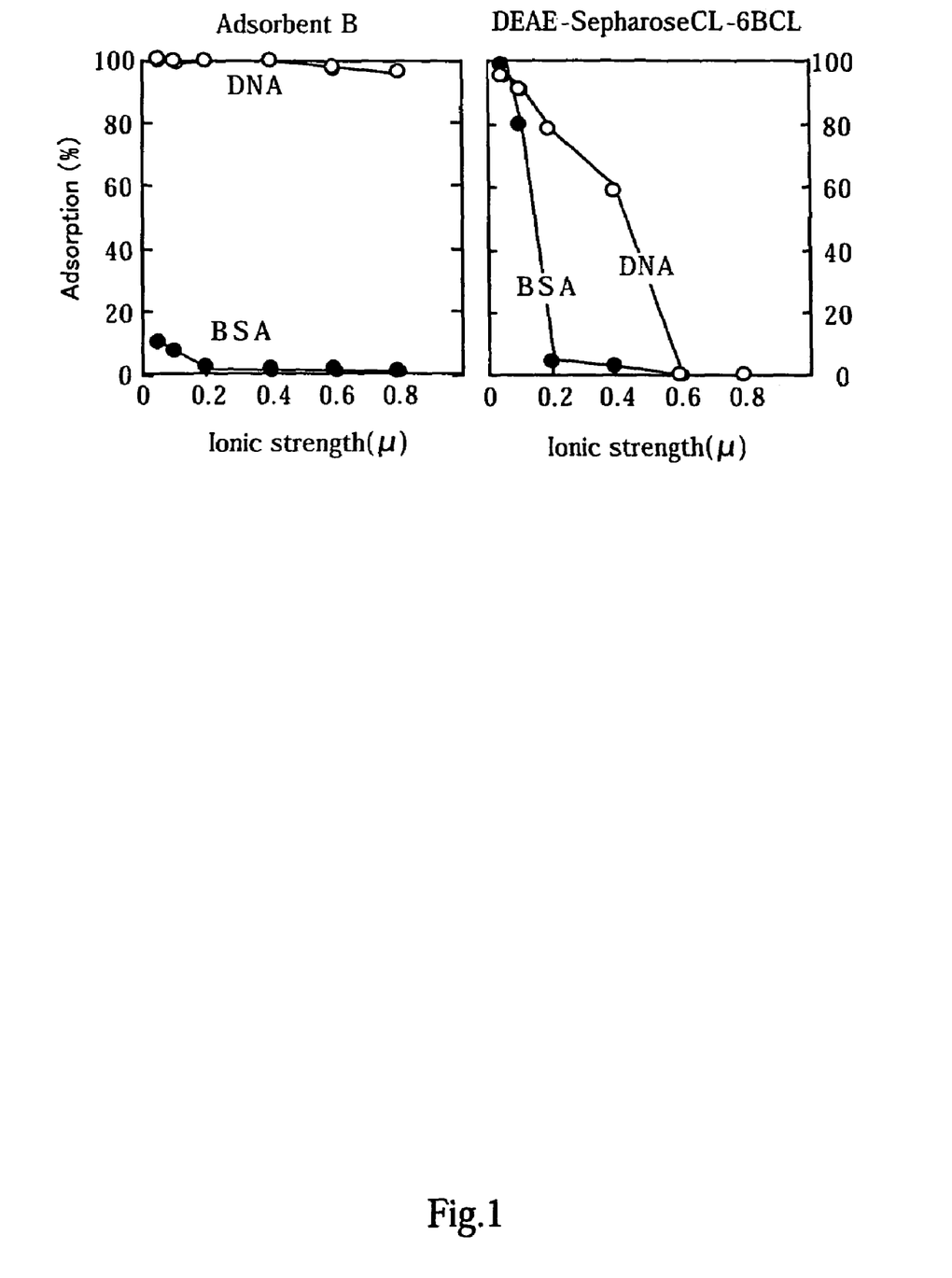
FIG. 1 is a graph showing the results obtained by examining ionic strength dependence of the adsorption of DNA to adsorbent B in one example according to the present invention.

Ionic Strength Dependability of DNA Adsorption to the Adsorbent 0.4 mL of adsorbent B equilibrated with phosphate buffer at each ionic strength (0.1, 0.2, 0.4, 0.6, and 0.8) and 4.0 mL of sample solution (containing 500 μg/mL BSA and 10 μg/mL DNA) were mixed in a tube, followed by stirring at 25° C. for 2 hours. Subsequently, the DNA and BSA concentrations of the supernatant obtained by centrifugation were measured. The results as shown in FIG. 1 indicate that an ionic strength of 0.4 or less results in an almost 100% adsorption of DNA to the adsorbent and an ionic strength of 0.2 or more results in an almost 0% adsorption of BSA to the absorbent. Therefore, a preferred ionic strength for washing of the adsorbent with nucleic acids attached on the adsorbent is 0.2 to 0.4.

COMPARATIVE EXAMPLE

Nucleic acids were removed by a batch method using DEAE-Sepharose CL-6B (an ion exchanger from Amersham Biosciences). DEAE-Sepharose CL-6B (0.50 g) was mixed with 10 mL of phosphate buffer at each ionic strength (0.1, 0.2, 0.4, 0.6, and 0.8), followed by stirring at room temperature for 10 min. After equilibration in this manner, the ion exchanger was recovered by filtration. This DEAE-Sepharose CL-6B; a solution of nucleic acid (DNA; 50 μg) in phosphate buffer (5 mL); and a solution of bovine serum albumin (BSA; 2500 μg) in phosphate buffer (5 mL), which had the same ionic strength as each ionic strength mentioned above, were mixed and stirred at 25° C. for 2 hours. After stirring, the concentration of DNA in the supernatant was measured.

The results as shown in FIG. 1 indicated that at every ionic strength used, DEAE-Sepharose CL-6B is lower both in DNA adsorption capacity and in DNA selective adsorption, demonstrating that adsorbent B is superior to DEAE-Sepharose CL-6B.

Example 9

Recovery of DNA from the Adsorbent

Figure 2:
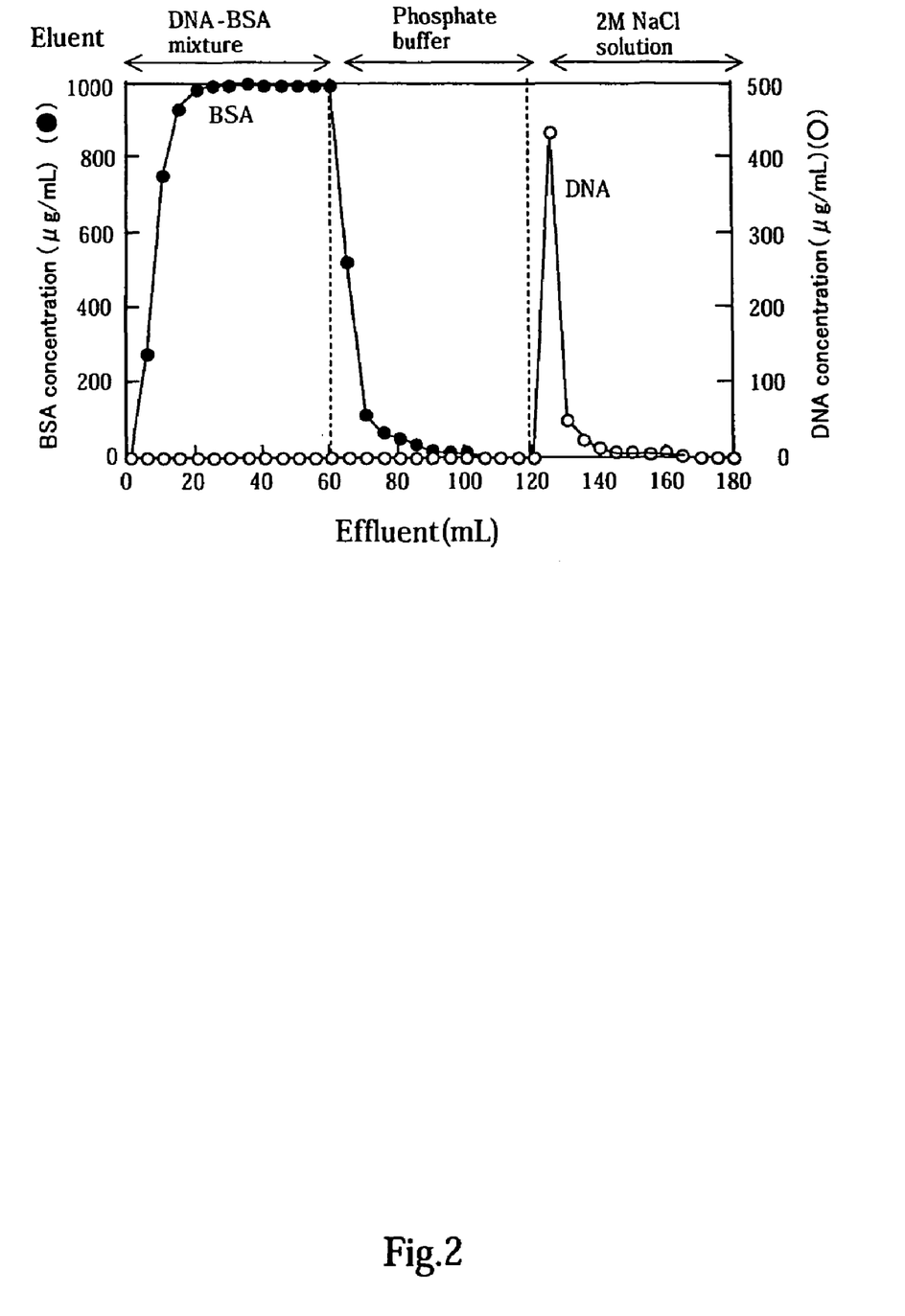
FIG. 2 is a graph showing the BSA and DNA concentrations measured in each of the column effluent fractions collected in 5 mL aliquots when DNA is recovered by being adsorbed to adsorbent A in one example according to the present invention.

In the same manner as in Example 4, the column (diameter: 4.6 mm, length: 100 mm) packed with adsorbent A (1.66 mL) was equilibrated by passing phosphate buffer (0.2 of ionic strength, pH 7.0) through. To this were added 60 mL of the mixed solution of DNA (100 μg/mL) and BSA (1,000 μg/mL), 60 mL of phosphate buffer, and 60 mL of 2M sodium chloride aqueous solution. effluent was collected in 5 mL fractions and the BSA and DNA concentrations in each fraction were measured and plotted on a graph. The results are shown in FIG. 2.

First, when the DNA-BSA mixure was passed through the column, the BSA concentration added and elution concentration were equilibrated after 20 mL of elution. Meanwhile, adsorption of DNA added was almost 100%.

Next, when 60 mL of phosphate buffer was passed through the column, only BSA was eluted. BSA was no longer eluted at the point of addition of about 40 mL (BSA recovery: 90%).

Next, when 2M sodium chloride aqueous solution was passed through the column, only DNA was eluted (recovery: 49%). These results suggest that use of the adsorbent enables efficient recovery of DNA and that the adsorbent according to the present invention is useful for recovery of DNA.

Example 10

Ionic Strength Dependence in the Recovery of DNA

Figure 3:
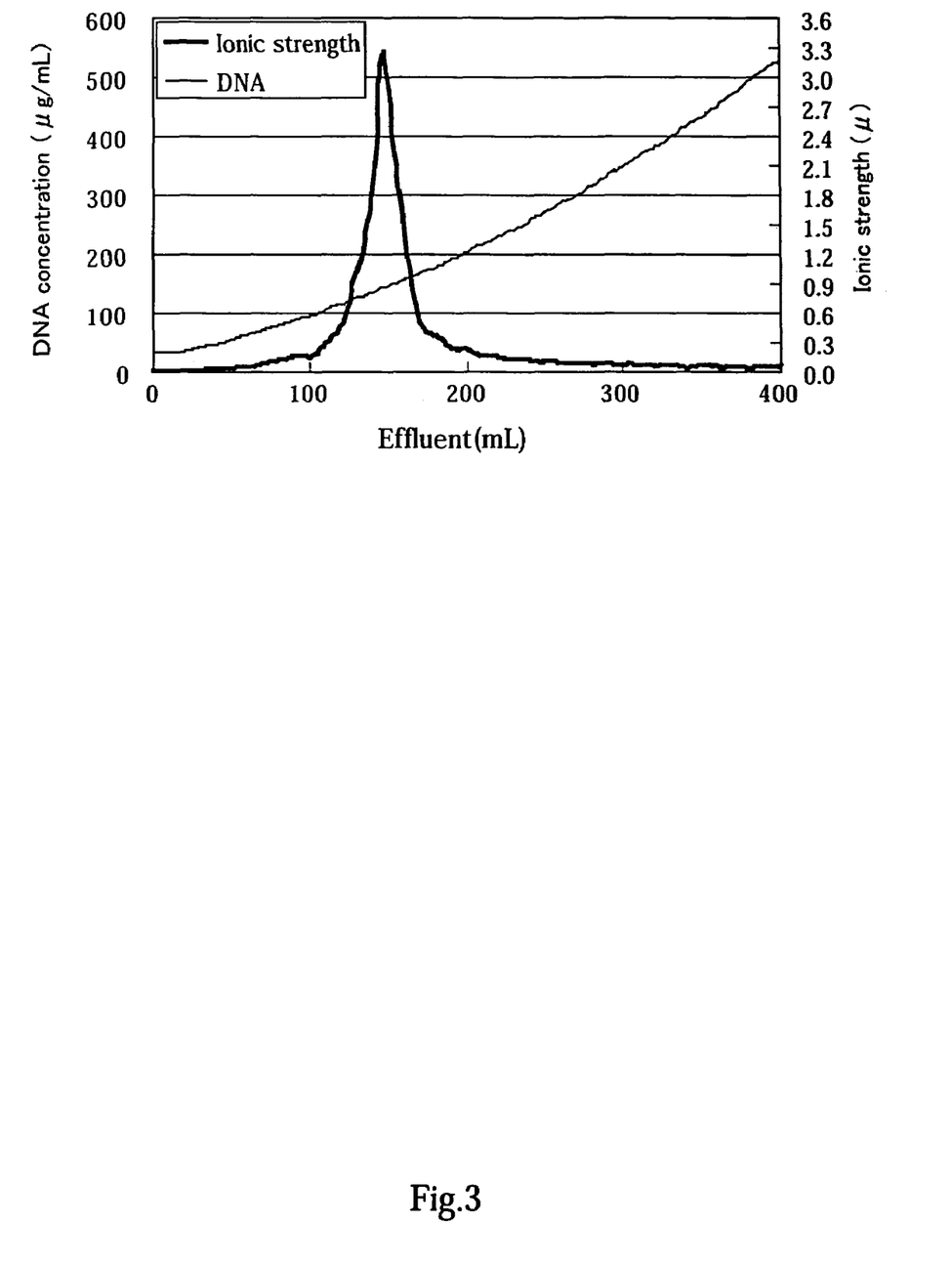
FIG. 3 is a graph showing ionic strength dependence of DNA dissociation when DNA is dissociated from adsorbent A in one example according to the present invention.

The column (diameter: 9.0 mm, length: 100 mm) packed with adsorbent A (6.36 mL) was equilibrated by passing phosphate buffer (0.2 of ionic strength, pH 7.0) through. 250 mL of a solution of DNA (100 μg/mL) and 250 mL of phosphate buffer were passed through the column, followed by passing 600 mL of elution buffer through at a flow rate of 1.0 mL/min such that the ionic strength was 0.2 to 3.2. The volume, DNA concentration, and ionic strength of the effluent were measured and plotted on a graph. FIG. 3 shows the results obtained after the ionic strength was increased. Ionic strength was calculated by measuring electric conductivity.

Elution of DNA started at an ionic strength of about 0.3, rapidly increased at about 0.6, reached its peak at about 0.9, sharply decreased at about 1.2, and ceased at about 3. Thus, recovery of DNA is enabled by setting ionic strength at 0.3 or more to 3.0 or less, more preferably at 0.6 or more to 1.2 or less.

Example 11

Regeneration and Reuse of the Nucleic Acid Adsorbent

In the same manner as in Example 9, the column (diameter: 4.6 mm, length: 100 mm) packed with adsorbent A (1.66 mL) was equilibrated by phosphate buffer. DNA was adsorbed by passing 180 mL of DNA phosphate buffer solution at 50 μg/mL through the column, which was then washed by passing 60 mL of phosphate buffer through. This was followed by elution of DNA by passing 60 mL of 2M NaCl aqueous solution (DNA recovery: 49%) through the column.

Subsequently, the column was regenerated by dissociating DNA from the adsorbent by passing 50 mL of 0.2M NaOH (pH 13) through, followed by equilibration with phosphate buffer. Adsorption and recovery of DNA were performed again in the same manner.

Figure 4:
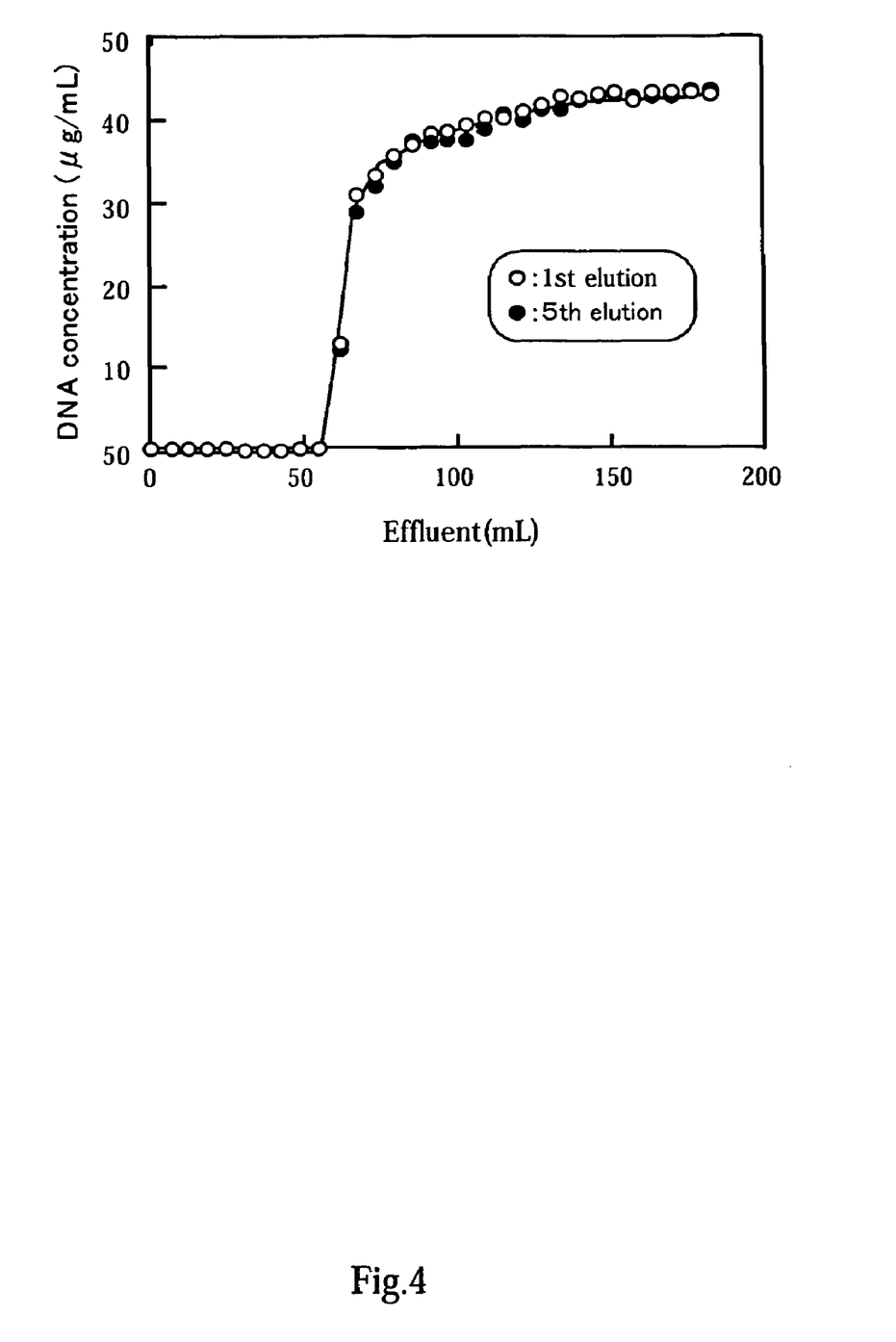
FIG. 4 is a graph showing the results of comparison of DNA adsorption property between the first run and the fifth run when the operation of DNA adsorption to adsorbent A was repeated 5 times in one example according to the present invention.

This DNA re-adsorbing operation was repeated 5 times. As shown in FIG. 4, there was no change in DNA adsorption property between the first run and the fifth run (recovery in the fifth run: 53%). These results indicate that the nucleic acid adsorbent according to the present invention can be regenerated and reused at least 5 times.

Example 12

Removal of DNA from Crushed Yeast Extract

To investigate whether the adsorbent according to the present invention is capable of selectively adsorbing nucleic acids from complex mixtures such as cell extract, the following experiment was performed in the same manner as in Example 9. Each adsorbent was packed into a 1 mL column (diameter: 9 mm, length: 16 mm), which was equilibrated with 0.02 M phosphate buffer (pH 7.2, ionic strength μ=0.17). Subsequently, 20 mL of a yeast crushed extract (total proteins 2.2 mg/mL, DNA 160 μg/mL, 0.02 M phosphate buffer solution) was passed through the column (25° C., flow rate: 0.1 mL/min), followed by washing the column with 20 mL of phosphate buffer (pH 7.2, ionic strength μ=0.17). By measuring proteins and DNA concentrations in total effluent obtained here, the protein recovery and DNA adsorption were investigated. The results are shown in Table 1. Crushing and extraction of yeast were performed using the ultrasonic crushing and extraction method (H. Maemura, S. Morimura, K. Kida, J. Inst. Brew, 104, 207-211, 1998). In addition, as a comparative experiment, an experiment was performed using DEAE-Sepharose CL-6B (column volume: 1 mL, dry weight: 0.05 g), and cross-linked PAA particles (PAA-B) (column volume: 1 mL, dry weight: 0.5 g) in place of the adsorbents.

TABLE 1

|  | DNA adsorption (%) | Protein recovery (%) |
|---|---|---|
| Adsorbent A | 99 | 97 |
| Adsorbent B | 99 | 94 |
| DEAE-Sepharose CL-6B | 22 | 96 |
| Cross-linked PAA particles (PAA-B) | 78 | 87 |

In conclusion, the adsorbent according to the present invention can efficiently and selectively adsorb nucleic acids from complex mixtures, such as cell extract. Accordingly, the adsorbent according to the present invention is also useful in recovering nucleic acids from complex mixtures, such as cell extract.

Thus, according to the embodiments of the present invention, a nucleic acid adsorbent capable of selectively and efficiently adsorbing nucleic acids; methods for adsorbing, removing, dissociating, and recovering nucleic acids using the same; and a method for regenerating the same after use can be provided. More specifically, a nucleic acid adsorbent capable of selectively and efficiently adsorbing nucleic acids from complex mixtures, such as cell extract; methods for adsorbing, removing, dissociating, and recovering nucleic acids using the same; and a method for regenerating the same for complex mixtures, such as cell extract, after use, can be provided.

What is claimed is:

1. A nucleic acid adsorbent for adsorbing a nucleic acid contained in cell extract,
   wherein a polymer comprising a constitutional unit represented by the following formula (I) is immobilized on a water-insoluble carrier, wherein $R_1$ represents hydrogen, fluoride, or methyl; $R_2$ and $R_3$ each independently represent alkyl of 1 to 6 carbon atoms; A represents —NH— or —O—; and B represents alkylene of 2 to 18 carbon atoms.

2. The nucleic acid adsorbent of claim 1, wherein, in formula (I), $R_1$ represents hydrogen or methyl; $R_2$ and $R_3$ each independently represent methyl, ethyl, or propyl; A represents —NH— or —O—; and B represents alkylene of 2 to 6 carbon atoms.

3. The nucleic acid adsorbent of claim 1, wherein, in formula (I), $R_1$ represents hydrogen or methyl; $R_2$ and $R_3$ each independently represent methyl or ethyl; A represents —NH— or —O—; and B represents propylene.

4. The nucleic acid adsorbent of claim 1, wherein, in formula (I), $R_1$ represents hydrogen; $R_2$ and $R_3$ represent methyl; A represents —NH—; and B represents propylene.

5. The nucleic acid adsorbent of claim 1, wherein, in formula (I), $R_1$ represents methyl; $R_2$ and $R_3$ represent methyl; A represents —NH—; and B represents propylene.

6. A nucleic acid adsorbent for adsorbing a nucleic acid contained in cell extract,
   wherein a polymer formed from one monomer represented by the following formula (II) is immobilized on a water-insoluble carrier, wherein $R_1$ represents hydrogen, fluoride, or methyl; $R_2$ and $R_3$ each independently represent alkyl of 1 to 6 carbon atoms; A represents —NH— or —O—; and B represents alkylene of 2 to 18 carbon atoms.

7. A nucleic acid adsorbent for adsorbing a nucleic acid contained in cell extract,
   wherein a polymer formed from a mixture comprising at least one monomer represented by the following formula (II) is immobilized on a water-insoluble carrier, herein $R_1$ represents hydrogen, fluoride, or methyl; $R_2$ and $R_3$ each independently represent alkyl of 1 to 6 carbon atoms; A represents —NH— or —O—; and B represents alkylene of 2 to 18 carbon atoms.

8. The nucleic acid adsorbent of claim 7, wherein, in formula (II), $R_1$ represents hydrogen or methyl; $R_2$ and $R_3$ each independently represent methyl, ethyl, or propyl; A represents —NH— or —O—; and B represents alkylene of 2 to 6 carbon atoms.

9. The nucleic acid adsorbent of claim 7, wherein, in formula (II), $R_1$ represents hydrogen or methyl; $R_2$ and $R_3$ represent methyl; A represents —NH— or —O—; and B represents alkylene of 2 to 6 carbon atoms.

10. The nucleic acid adsorbent of claim 7, wherein, in formula (II), $R_1$ represents hydrogen; $R_2$ and $R_3$ represent methyl; A represents —NH—; and B represents propylene.

11. The nucleic acid adsorbent of claim 7, wherein, in formula (II), $R_1$ represents methyl; $R_2$ and $R_3$ represent methyl; A represents —NH—; and B represents propylene.

12. The nucleic acid adsorbent of claim 7, wherein the polymer formed from the mixture further comprising at least one monomer represented by the following formula (III) is immobilized on the water-insoluble carrier, wherein, $R_4$ represents hydrogen or methyl; $R_5$, $R_6$, and $R_7$ each independently represent alkyl of 1 to 3 carbon atoms, D represents —NH— or —O—, E represents alkylene of 2 to 6 carbon atoms, and X represents fluoride, chlorine, bromine, iodine, $1/2SO_4$, $1/3PO_4$, $1/2CO_3$, or $NO_2$.

13. The nucleic acid adsorbent of claim 7, wherein the polymer formed from the mixture further comprising at least one monomer represented by the following formula (IV) is immobilized on the water-insoluble carrier, wherein $R_8$ represents hydrogen or methyl; $R_9$ represents alkyl of 1 to 3 carbon atoms; G represents —NH—, —$NR_{10}$—, or —O—; and $R_{10}$ represents alkyl of 1 to 3 carbon atoms.

14. The nucleic acid adsorbent of claim 1 or 7, wherein the polymer is immobilized on the water-insoluble carrier with a crosslinker.

15. The nucleic acid adsorbent of claim 14, wherein the crosslinker is epichlorohydrin.

16. The nucleic acid adsorbent of claim 1 or 7, wherein the water-insoluble carrier is in the form of a sphere, hollow fiber, or membrane.

17. The nucleic acid adsorbent of claim 1 or 7, wherein the water-insoluble carrier is cellulose.

18. The nucleic acid adsorbent of claim 17, wherein the cellulose is a spherical particle.

19. The nucleic acid adsorbent of claim 1 or 7, wherein the cell extract is yeast extract.

20. A method for adsorbing a nucleic acid contained in cell extract,
wherein the nucleic acid adsorbent of claim 1 or 7 is mixed with a solution containing a nucleic acid.

* * * * *

UNITED STATES PATENT AND TRADEMARK OFFICE
CERTIFICATE OF CORRECTION

PATENT NO. : 7,358,050 B2 Page 1 of 1
APPLICATION NO. : 11/214773
DATED : April 15, 2008
INVENTOR(S) : Chuichi Hirayama et al.

It is certified that error appears in the above-identified patent and that said Letters Patent is hereby corrected as shown below:

1. On the title page of the patent, the first line of item (75) should read --Kumamoto (JP)-- to the right of the name of inventor Chuichi Hirayama. Instead, it reads "Kmamoto."

2. Column 18, line 44, in claim 7, should read --wherein $R_1$ represents ...,-- but instead reads "herein $R_1$ represents ...."

Signed and Sealed this

Fourth Day of November, 2008

JON W. DUDAS
*Director of the United States Patent and Trademark Office*